United States Patent
Gamel et al.

(10) Patent No.: US 8,890,075 B2
(45) Date of Patent: Nov. 18, 2014

(54) MEASURING CELL FOR THE INFRARED ANALYSIS OF FLUIDS, MEASURING SYSTEM HAVING SUCH A MEASURING CELL, AND METHOD FOR PRODUCING SUCH A MEASURING CELL

(75) Inventors: Frédéric Julien Gamel, Bettinglés-Saint-Avoid (FR); Wolfgang Kurt Brode, Hermsdorf (DE); Horst Mannebach, Münstermaifeld (DE); Frank Herold, Saarbrucken (DE); Indira Käpplinger, Jena (DE)

(73) Assignee: Hydac Electronic GmbH, Saarbrücken (DE)

( * ) Notice: Subject to any disclaimer, the term of this patent is extended or adjusted under 35 U.S.C. 154(b) by 367 days.

(21) Appl. No.: 13/261,198

(22) PCT Filed: Sep. 14, 2010

(86) PCT No.: PCT/EP2010/005629
§ 371 (c)(1),
(2), (4) Date: Feb. 29, 2012

(87) PCT Pub. No.: WO2011/054412
PCT Pub. Date: May 12, 2011

(65) Prior Publication Data
US 2012/0174658 A1   Jul. 12, 2012

(30) Foreign Application Priority Data
Oct. 27, 2009  (DE) .......................... 10 2009 051 853

(51) Int. Cl.
*G01J 5/02* (2006.01)
*B01L 3/00* (2006.01)
(Continued)
CPC ............... *B01L 3/502707* (2013.01); *B81C 1/00119* (2013.01); *G01N 21/0317* (2013.01); *G01N*
(Continued)

(52) U.S. Cl.
(58) Field of Classification Search
CPC .............................. G01N 1/3504; G01N 21/61
USPC .......................................................... 250/343
See application file for complete search history.

(56) References Cited

U.S. PATENT DOCUMENTS 4,834,534 A    5/1989  Wiget
7,344,499 B1 *  3/2008  Prausnitz et al. ............. 600/309
(Continued)

FOREIGN PATENT DOCUMENTS

AT          500 075        10/2007
DE        41 37 060 A1     5/1993
(Continued)

OTHER PUBLICATIONS

L. Brusberg, Thin Glass Based Packaging Technologies for Optoelectronic Modules, Proc. 2009 Electronic Components and Technology Conference, IEEE, May 25, 2009, 207-212.

(Continued)

*Primary Examiner* — David Porta
*Assistant Examiner* — Mindy Vu
(74) *Attorney, Agent, or Firm* — Roylance, Abrams, Berdo & Goodman LLP

(57) ABSTRACT

A measuring cell (1) for the infrared analysis of fluids, in particular a measuring cell (1) having a permissible operating pressure of more than 20 bar and preferably more than 50 bar, has a flow channel (10) for the fluid formed between first and second elements (2, 4). Each element is transparent to infrared radiation at least in some sections. The infrared radiation can be radiated into the flow channel (10) by the first element (2) and can exit the flow channel (10) by the second element (4). The two elements (2, 4) are connected to each other in a fluid-tight and mechanically high-strength manner by a connecting layer (6) arranged between them and made of a glass-containing material, in particular a sintered glass-ceramic material. A measuring system (8) has that measuring cell (1). A method produces that measuring cell (1).

25 Claims, 5 Drawing Sheets

(51) Int. Cl.
*B81C 1/00* (2006.01)
*G01N 21/03* (2006.01)
*G01N 21/05* (2006.01)
*G01N 21/35* (2014.01)

(52) U.S. Cl.
CPC ......... 21/05 (2013.01); *G01N 21/03* (2013.01); *G01N 21/3577* (2013.01); *B01L 2200/0636* (2013.01); *B01L 2200/0689* (2013.01); *B01L 2200/12* (2013.01); *B01L 2300/0663* (2013.01); *B01L 2300/0887* (2013.01); *B81B 2201/058* (2013.01); *B81C 2203/032* (2013.01); *G01N 21/35* (2013.01); *G01N 2021/056* (2013.01); *G01N 2021/0346* (2013.01)
USPC ......................................................... 250/343

(56) References Cited

U.S. PATENT DOCUMENTS

| 2002/0063330 A1 | 5/2002 | Macris |
| 2011/0223654 A1* | 9/2011 | Holman et al. ............ 435/288.7 |

FOREIGN PATENT DOCUMENTS

| DE | 41 37 060 C2 | 5/1993 |
| DE | 44 12 012 | 10/1995 |
| DE | 197 31 241 | 2/1999 |
| DE | 199 09 692 | 3/2000 |
| DE | 101 04 957 | 3/2002 |
| DE | 102 44 786 | 4/2004 |
| DE | 103 21 472 | 12/2004 |
| DE | 103 29 866 | 1/2005 |
| DE | 10 2004 008 685 | 9/2005 |
| EP | 0 488 947 | 6/1992 |
| GB | 2341925 | 3/2000 |
| JP | 61130855 | 6/1986 |

OTHER PUBLICATIONS

P. Bembnowicz and L. J. Golonka, Integration of transparent glass window with LTCC technology for μTAS application, Journal of the European Ceramic Society, Oct. 4, 2009.

T. Mülln et al., Optical-fluidic Sensors in LTCC-Technology, Proc. 2007 Intl. Students and Young Scientists Workshop "Potonics and Microsystems," Jul. 8, 2007.

M. Fischer et al., "Silicon on Ceramics—A New Concept for Micro-Nano-Integration on Wafer Level," Proc. NSTI Nanotech, Jun. 1, 2008, 157-160.

M. Fischer et al., "Silicon on Ceramics—A New Integration Concept for Silicon Devices to LTCC," Journal of Microelectronics and Electronic Packaging, Jan. 1, 2009, vol. 6, 1-5.

* cited by examiner

MEASURING CELL FOR THE INFRARED ANALYSIS OF FLUIDS, MEASURING SYSTEM HAVING SUCH A MEASURING CELL, AND METHOD FOR PRODUCING SUCH A MEASURING CELL

FIELD OF THE INVENTION

The invention relates to a measuring cell for the infrared analysis of fluids, a measuring system having such a measuring cell, and a method for producing such a measuring cell.

BACKGROUND OF THE INVENTION

A measuring cell of this type can be used, for example, for the analysis of oils used in technical systems for the transmission of pressures, for lubrication, and/or for cooling. In operation, the oil is subjected to aging and/or fouling. For the operational reliability of the system, it is critical to be able to check the quality state of the oil in near real time. For this purpose, the wavelength-dependent transmission of the oil can be measured, or the absorption bands can be measured especially in the infrared range. Conclusions can be drawn from those measurements regarding the quality of the oil.

Reflection spectrometers with these measuring cells are known, for example, from DE 103 21 472 A1, DE 197 31 241 C2, or EP 0 488 947 A1. Transmission spectrometers are known, for example, from DE 10 2004 008 685 A1 and GB 2 341 925 A.

DE 41 37 060 C2 discloses a microcell for infrared spectroscopy.

U.S. Patent Publication No. 2002/0063330 A1 discloses a heat sink and a method for producing this heat sink.

DE 102 44 786 A1 and AT 500 075 B1 disclose a method for connecting wafers. DE 103 29 866 A1 discloses the use of wafer bonding for a piezoelectric substrate with temperature compensation and method for producing a surface wave component.

DE 199 09 692 C1 discloses a flow measuring cell for studying a high-speed chemical reaction.

DE 101 04 957 A1 discloses a method for producing a three-dimensional micro flow cell.

SUMMARY OF THE INVENTION

An object of the invention is to provide a measuring cell with improved performance characteristics, as well as a pertinent measuring system and a pertinent production method. The measuring cell and the sensor and emitter are designed to be used even for high operating pressures. For this purpose they are to exhibit high operational reliability.

The object is basically achieved by a measuring cell for the infrared analysis of fluids, especially by a measuring cell with an allowable operating pressure of more than 20 bar and preferably more than 50 bar, with a flow channel for the fluid formed between a first transparent element and a second transparent element. Each element is transparent at least in sections to infrared radiation. The infrared radiation can be irradiated into the flow channel via the first element and can exit from the flow channel via the second element. The two elements are connected fluid-tight to one another with high mechanical strength by a connecting layer of glass-containing material, especially of a sintered glass-ceramic material, which layer is located between the two elements.

Advantageously, even comparatively thick elements, as are necessary for the high pressure use, can be permanently and reliably connected to one another by the connecting layer. Especially that connection can be produced without porous spots in spite of the stiffness of the elements that are comparatively thick with respect to high pressure use. In the still unsintered state, by applying a corresponding pressure, the material of the connecting layer can be brought into contact with the surfaces of the two elements such that a topography or ripple of the surfaces of the two elements that may be present is equalized in this way. This arrangement is especially advantageous when the measuring cells are fabricated in a panel; i.e., boards or wafers on which a plurality of elements, and thus, a plurality of measuring cells are implemented at the same time are used, for example, for the components.

For example, the elements in a panel can be formed from a silicon wafer with a thickness of more than 1 mm, especially more than 1.5 mm and preferably more than 2 mm. The connecting layer in the sintered state can have a thickness of more than 50 μm and less than 500 μm, especially more than 100 μm and less than 300 μm, and preferably more than 120 μm and less than 200 μm. The flow channel for the fluid can be a microfluid channel with a length of more than 3 mm, especially more than 6 mm and preferably more than 9 mm, and with a width of less than 10 mm, especially less than 8 mm and preferably less than 6 mm. In the flow channel, there can be one or more spacers by which even under the effect of high pressure the height of the flow channel is kept to a definable value. The spacers can be formed, for example, by webs extending lengthwise to the flow direction. The spacers and/or the geometry of the flow channel can be formed at least in sections by one of the elements and/or by the connecting layer.

The connecting layer can be applied structured to one of the elements or placed between the two elements. By structuring the connecting layer, for example, the flow channel can be defined. Particularly the two elements bordering the flow channel can also be fundamentally unstructured. Alternatively or in addition, the two elements can also have, at least in sections, a structure defining the flow channel and produced by etching onto the surface. Fundamentally, the connecting layer can also be applied by all methods that are known, for example, from thick film technology.

The connecting layer in the form of a strip, a tape, or a membrane can be laminated onto one of the elements or laminated between the two elements. For example, the connecting layer in membrane form can be placed on a wafer forming the first elements of a plurality of measuring cells. A wafer forming the second elements of the plurality of measuring cells can be placed on the connecting layer. Then, the combination can be pressed together and then sintered.

The connecting layer can have exit channels for the exit of organic components from the connecting layer in a process that precedes the sintering. The exit channels can be formed by a lattice-like structure of the connecting layer. Providing these exit channels is especially advantageous in the production of the measuring cells in a panel, because in this case the organic components that are volatile in temperature treatment can emerge laterally.

The connecting layer can be formed from a low-temperature cofired ceramic, preferably having plasticizers. A lamination of the connecting layer by the plasticizers is possible. In the not yet sintered state, the connecting layer is flexible. Components of the connecting layer in this state can be glass, especially borosilicate glass, borofloat glass, and/or quartz glass, ceramic—for example Al2O3—and organic components that volatilize during setting. The mixing of these components ensures the matching of the coefficient of thermal expansion in the temperature range from −50 to +850° C. to the coefficient of thermal expansion of the elements of the measuring cell, especially to the coefficient of thermal expansion of silicon.

The connecting layer in a temperature range between 0 and 200° C., especially between 0 and 400° C. and preferably between 0 and 600° C., can have a coefficient of linear thermal expansion which deviates less than 8 ppm/K, especially less than 5 ppm/K and preferably less than 0.5 ppm/K from the coefficient of linear thermal expansion of at least one of the elements, preferably of the two elements. In this way, good matching of the coefficient of thermal expansion from the connecting layer to the element is ensured so that the thermally induced stresses are low even in the sintered state of the measuring cell. Thus, a high operational reliability is guaranteed.

At least one of the two elements, on one surface forming the boundary for the flow channel, can have a surface structure that acts as an antireflection layer and/or filter layer for the infrared radiation and/or as adhesion promoter for the connecting layer. The transmission capacity of the measuring cell for infrared radiation can thus be significantly increased, as a result of which a high signal level arises for the evaluation of the sensor signal. Furthermore, in this way, an optical filter can also be integrated into the measuring cell. By that filter, the absorption bands of the fluid to be studied can be determined. In this way, the adhesive force of the connecting layer can be increased. This increase is especially advantageous in high pressure operation. The surface structure can be formed by a nanostructure on the surface.

The surface structure can have a plurality of needles with a density of more than 10,000 needles per $mm^2$, especially more than 100,000 needles per $mm^2$, and preferably more than 500,000 needles per $mm^2$. Such needle-shaped elements can be produced, for example, in single-crystalline silicon by self-masked dry etching. The surface structure produced in this way according to its optical appearance is also referred to as "black silicon."

The needles can have a length of more than 0.3 and less than 30 especially more than 0.5 and less than 15 µm, and preferably more than 0.8 and less than 8 Studies have shown that at this needle length, an especially favorable antireflection behavior for infrared radiation and/or a high adhesion to the connecting layer can be achieved.

One element can have the surface structure also in the region of the connecting layer. Advantageously, the surface structure, alternatively or in addition to its action as antireflection layer, is also used as an adhesion promoter for the connection of the element and the connecting layer. In particular, the needles can penetrate into the structure of the connecting layer. A large-area connecting layer is then formed by the high surface to volume ratio of the needles.

The two elements can be formed from single-crystalline silicon having a relatively high coefficient of transmission for infrared radiation and excellent mechanical properties. Moreover, the elements of single-crystalline silicon can be structured in almost any way with high precision to define flow channels, using known structuring methods from semiconductor technology, including dry chemical and wet chemical etching methods.

At least one of the two elements can have a thickness of more than 1 mm, especially more than 1.5 mm and preferably more than 2 mm. With such thick elements, especially in conjunction with the material single-crystalline silicon, measuring cells with high mechanical strength, that are thus also suitable for high pressure use, can be produced. The height of the flow channel defined by the thickness of the connecting layer can be between 50 and 500 µm, especially more than 80 µm and less than 400 µm, and preferably more than 100 µm and less than 300 µm.

The invention also relates to the structure of a measuring system for the infrared analysis of fluids by a measuring cell as described above with an emitter and a sensor. The measuring system has an emitter for the infrared radiation, for example, a broadband-emitting heat radiator and/or a comparatively narrowband-emitting infrared light emitting diode, and a receiver for the infrared radiation. Emitters and receivers are preferably located on opposite sides of the measuring cell. In one unit, the receiver can have several detector elements by which the intensity of the radiation in different wavelength ranges can be measured. For this purpose, the receiver can have several entry windows via which radiation is incident on one of the detector elements. The windows and/or the detector elements can enable filtering.

Likewise, several emitters with a narrowband emission can be used.

The measuring system can have an installation element with a receiving opening for the measuring cell. The measuring cell can be inserted into the receiving opening. The receiving opening can be adjusted with respect to its contour at least in sections to the outer contour of the measuring cell, which outer contour can be, for example, polygonal and/or especially rectangular. The installation element has one entry opening and one exit opening for the fluid. The fluid can enter the flow channel of the measuring cell via the entry opening. The fluid can emerge from the flow channel of the measuring cell via the exit opening.

The invention also relates to a method for producing a measuring cell, as described above. The connecting layer of glass-containing, especially glass-ceramic material, can be located between the two elements in the not yet sintered state, for example, in the form of a strip or a membrane. The connecting layer is a green compact. The connecting layer can have calibration markings or openings by which the connecting layer can be calibrated to the carrier of the elements. The connecting layer can be present in the form of an unsintered foil and/or can be made from a mixture of borosilicate glass, quartz glass, and aluminum oxide as well as organic solvents.

The connecting layer can be laminated as a green compact, for example, with a thickness of 300 µm under a pressure of 250 bar and at a temperature of 70° C., between the two wafers forming the elements.

The connecting layer under this loading flows through the plasticizers introduced in the green compact and equalizes all spacing tolerances between the two elements so that the connecting layer is in contact with the elements over the entire wafer surface.

The elements on their surface facing the connecting layer are nanostructured, for example, with the formation of needles. The needles penetrate into the structure of the connecting layer. The sintering process then takes place under the action of pressure and temperature. At a temperature starting from approximately 650° C., the glass frits are connected both to all components of the ceramic green compact and also to the needles of the wafers forming the elements. These needles are present in a nanostructure since in particular their lateral dimensions are very small. The application of pressure in the sintering process essentially prevents a lateral shrinkage of the connecting layer. The shrinkage of the connecting layer perpendicular to the surface of the wafers that form the elements can be about 50%.

Other objects, advantages and salient features of the present invention will become apparent from the following detailed description, which, taken in conjunction with the annexed drawings, discloses a preferred embodiment of the present invention.

BRIEF DESCRIPTION OF THE DRAWINGS

Referring to the drawings which form a part of this disclosure.

DETAILED DESCRIPTION OF THE INVENTION

Figure 1:
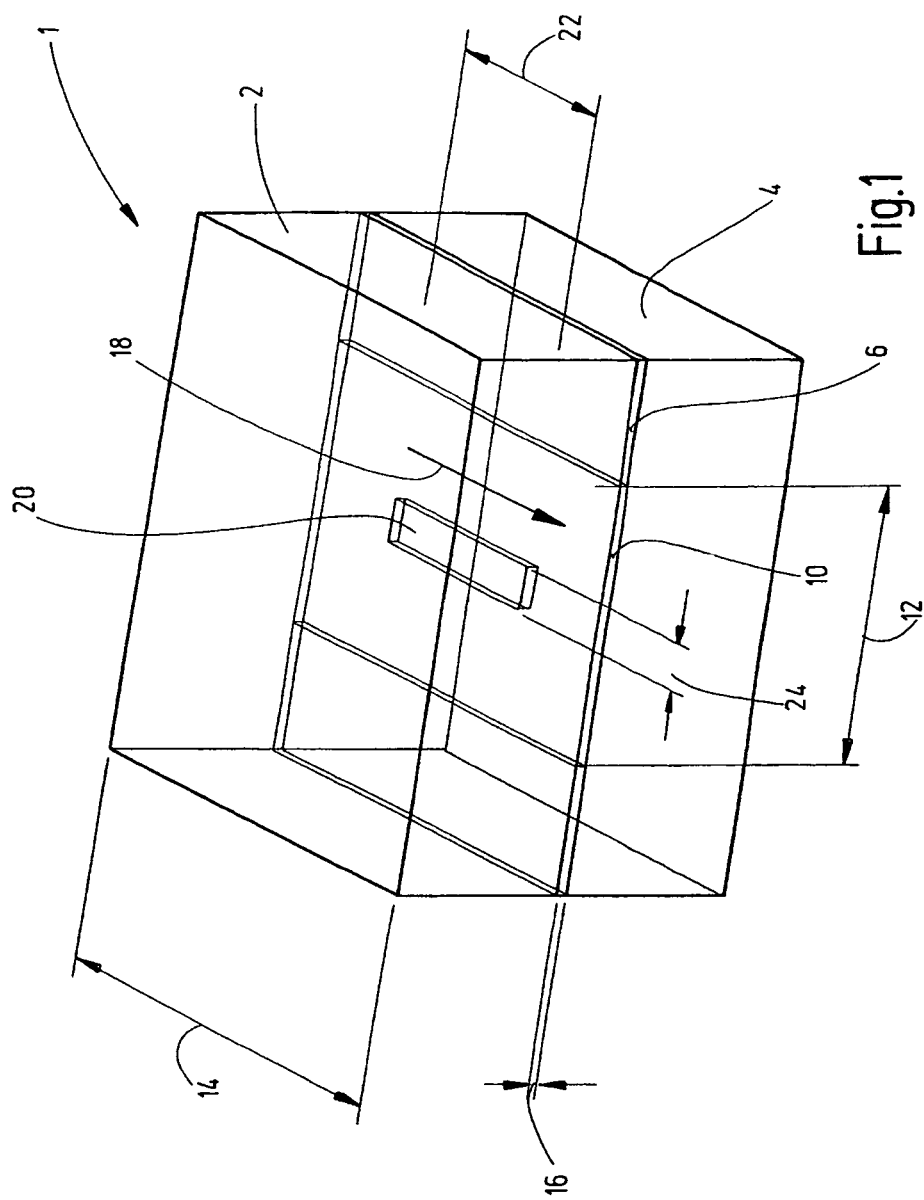
FIG. 1 is a perspective view of a measuring cell according to an exemplary embodiment of the invention.

FIG. 1 shows a perspective view of one exemplary embodiment of a measuring cell 1 according to the invention for the infrared analysis of fluids for high pressure operation. The flow channel 10 for the fluid in the exemplary embodiment has a width 12 of 5 mm, a length 14 of 9.5, and a height 16 of 0.2 mm. The flow direction is indicated by the arrow 18. In the flow direction 18 in the flow channel 10 in the middle with respect to the width 12, a spacer 20 extends and has a length 22 about 50% of the length 14 of the flow channel 10. In the exemplary embodiment, the spacer length is approximately 4.5 mm. The spacer width 24 is less than 20% of the width 12 of the flow channel 10, and in the exemplary embodiment is 0.8 mm. On the one hand, the flow channel height 16 is also stabilized in the middle region of the flow channel 10 by the spacer 20. The spacer 20 is made web-shaped and can be used to improve the laminar flow in the flow channel 10.

The flow channel 10 is formed between a first element 2 and a second element 4. The two elements are transparent to infrared radiation at least in sections and can be formed of single-crystalline silicon. Infrared radiation can be irradiated into the flow channel 10 via the first element 2. The infrared radiation can emerge from the flow channel via the second element 4. The two elements 2, 4 are connected to one another fluid-tight with high mechanical strength by a connecting layer 6 located in between. The connecting layer is formed of a glass-containing material, especially of a sintered glass ceramic material.

Figure 2:
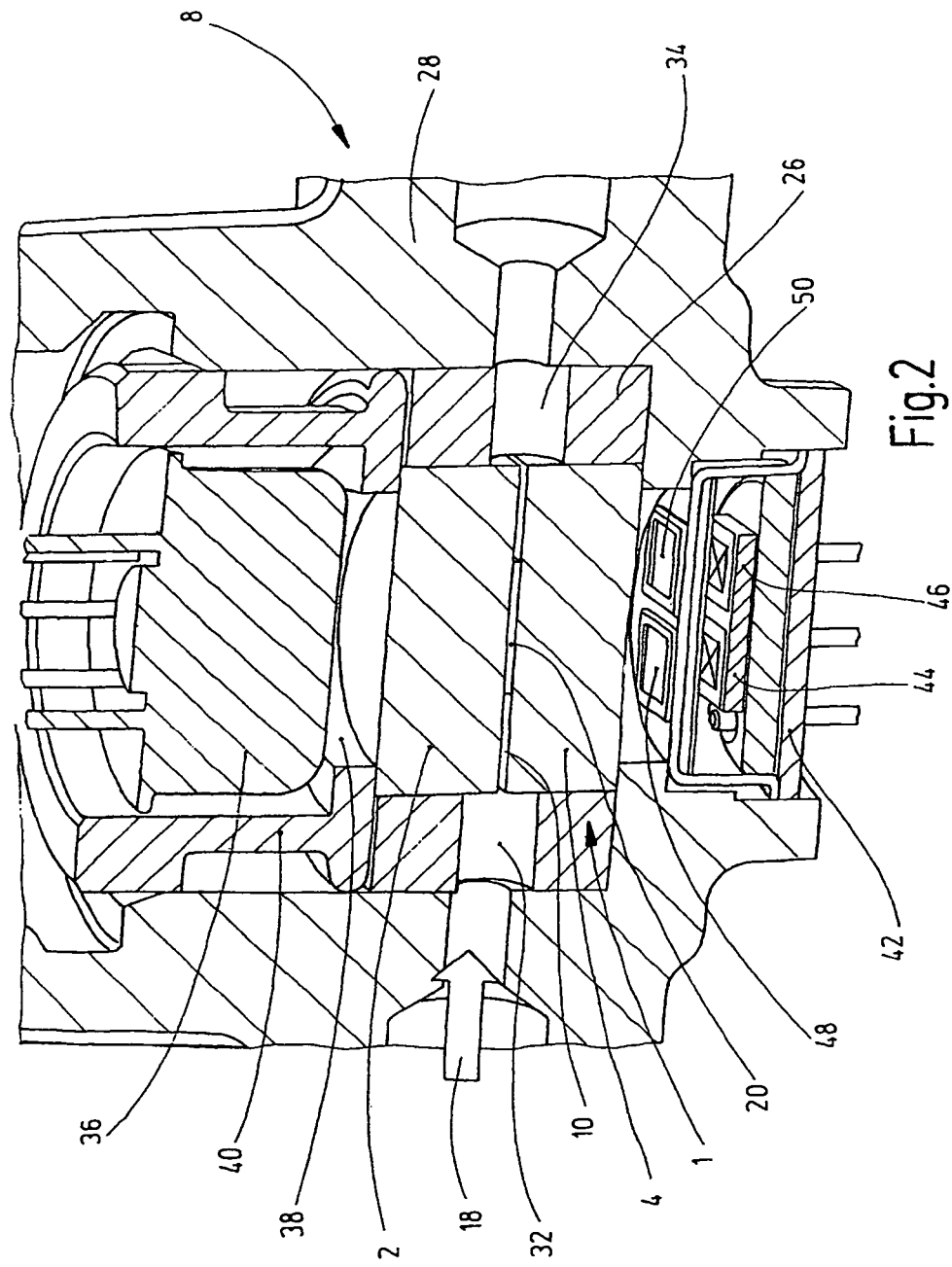
FIG. 2 is a side elevational view in section of a measuring system for the infrared analysis of fluids with the measuring cell of FIG. 1.
Figure 3:
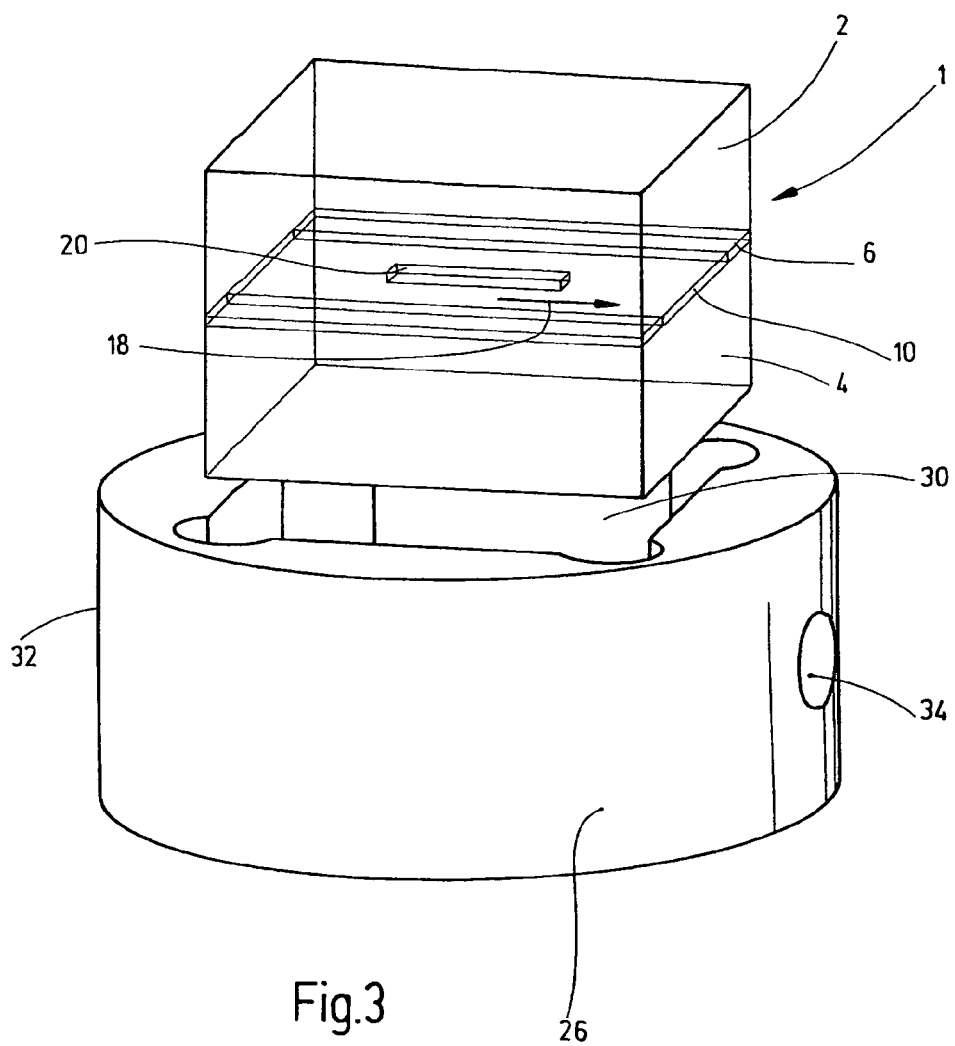
FIG. 3 is a perspective view of the installation element and measuring cell of FIG. 2.

FIG. 2 shows a section through a measuring system 8 for the infrared analysis of fluids with a measuring cell 1 as described above. The measuring cell 1 is arranged in a system housing 28 by an installation element 26. FIG. 3 shows a perspective view of the installation element 26 that has a receiving opening 30 into which the measuring cell 1 can be inserted. The receiving opening 30 is essentially matched to the outside contour of the measuring cell 1 that in turn is essentially rectangular, or in the special case, square. On its corners, the receiving opening 30 has bulges that facilitate the insertion of the measuring cell 1. The installation element 26 has an entry opening 32 and an exit opening 34 via which the fluid can enter the flow channel 10 of the measuring cell 1 or can emerge from the flow channel 10 of the measuring cell 1. The connection between the installation element 26 and the measuring cell 1 is fluid-tight. The sealing means which may be necessary for this purpose such as, for example, gaskets or the like are not shown in FIG. 2 for reasons of clarity.

The measuring system 8, on one side assigned to the first element 2 of the measuring cell 1, has an emitter 36 for infrared radiation. The emitter 36 can be, for example, a comparatively broadband-emitting heating element that in any case has a sufficient radiation intensity in the wavelength range of interest, for example, between 2 and 6 µm. The emitter 36 is preferably detachably fixed on the system housing 28 by a fastening element 40 having a central passage opening 38. The emitter 36 radiates essentially centrally onto the first element 2 of the measuring cell 1.

On the side opposite the measuring cell 1, in the measuring system 8, a receiver 42 is located opposite the outer surface of the second element 4 and preferably centrally with reference to the second element 4, and thus, to the measuring cell 1. In the illustrated exemplary embodiment, the receiver 42 has a total of four detector elements 44, 46, of which FIG. 2 shows only two detector elements 44, 46, as a result of the sectional view. On its surface facing the measuring cell 1, the receiver 42 has a total of four windows 48, 50 assigned to one detector element 44, 46 at a time. Each of the windows 48, 50 and/or each of the detector elements 44, 46 can have a filter layer so that only one narrowband region at a time of the infrared spectrum that has passed through the measuring cell 1 and that has been radiated from the emitter 36, is emitted onto the detector element 44, 46.

Figure 4:
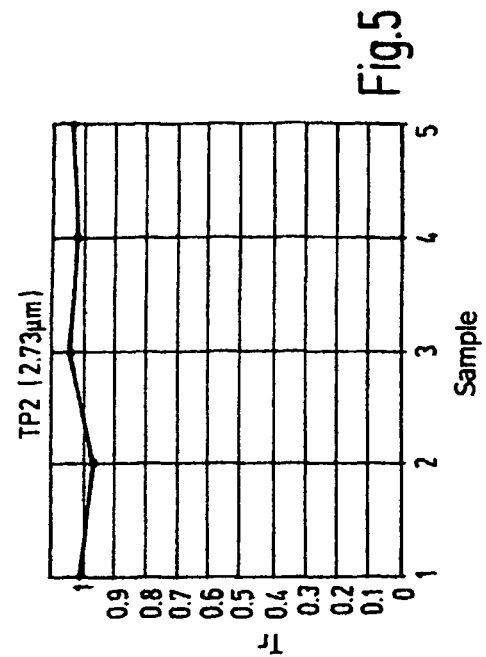
FIGS. 4 to 7 are graphs displaying the transmission behavior of a total of five fluid samples at four different wavelengths.
Figure 5:
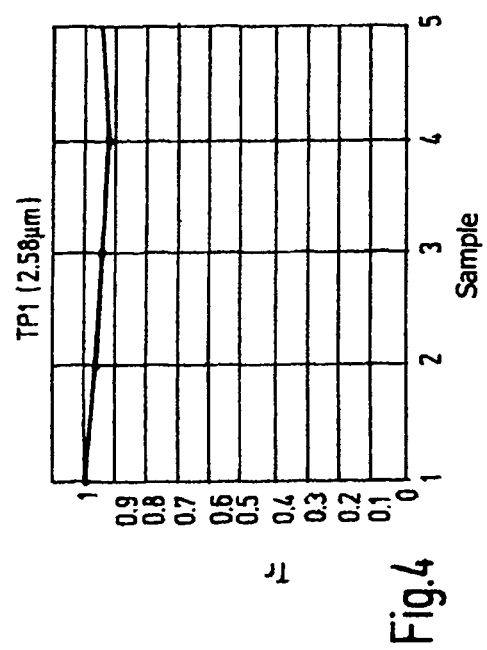
Figure 6:
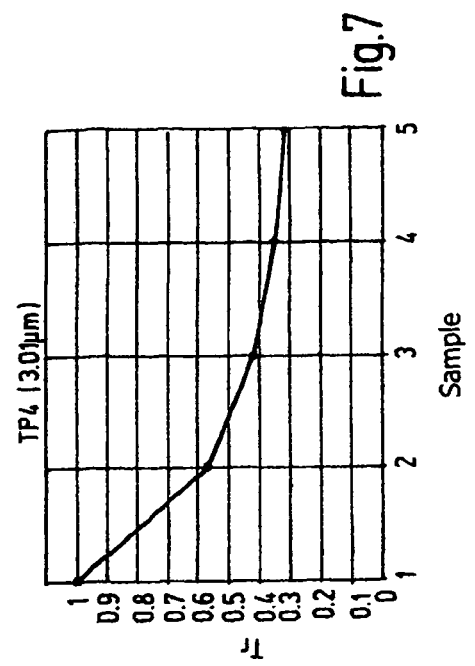
Figure 7:
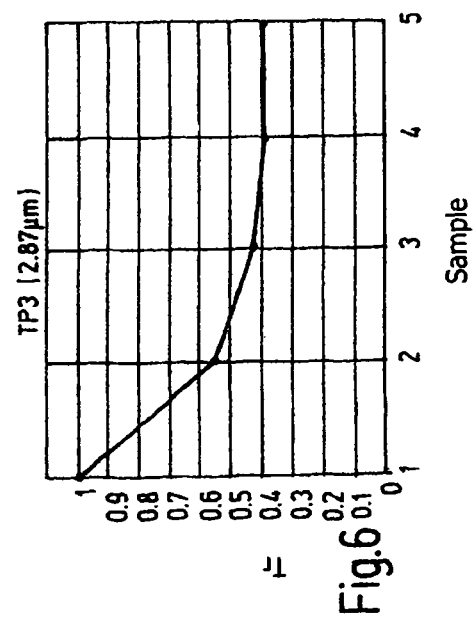

FIGS. 4 to 7 show the relative transmission behavior $T_r$ of a total of five fluid samples that are different with respect to their quality state at different wavelengths between 2.58 µm and 3.01 µm. Sample No. 1 is a fresh and still unused fluid, the aging increasing with the sample number. As FIGS. 4 and 5 show, at the wavelengths 2.58 and 2.73 µm, no aging-dependent absorptions of the fluid can be measured. Conversely, according to FIGS. 6 and 7, at the wavelengths 2.87 and 3.01 µm, aging-dependent absorptions occur, the wavelengths at which these absorption bands occur allowing conclusions regarding the aging-dictated components in the fluid. The circumstance that at certain wavelengths no aging-dictated absorption can be measured (FIGS. 4 and 5) permits using these wavelengths as reference bands in order, for example, to take a comparison measurement.

Figure 8:
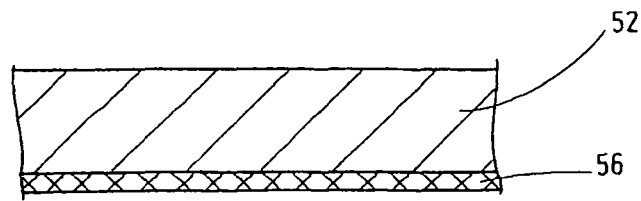
FIGS. 8 to 10 are partial, side elevational views in section illustrating different stages of the method for producing the measuring cell of FIG. 1.
Figure 9:
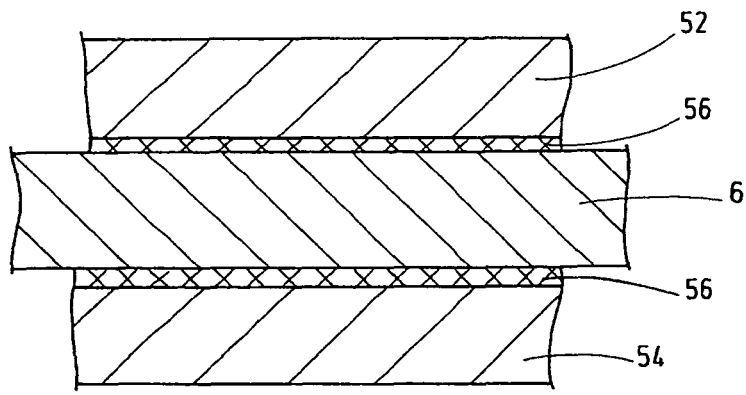
Figure 10:
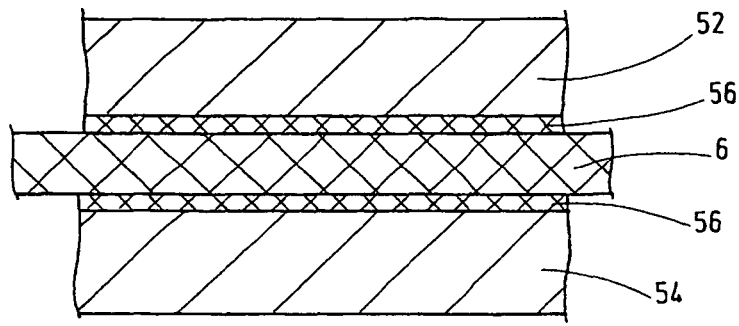

FIGS. 8 to 10 show different stages of the method for producing a measuring cell 1, as described above. For reasons of better representation, the dimensions are not shown to scale. First, a nanostructure 56, for example, a surface structure of a plurality of needles, is applied to the silicon wafers 52, 54 that form the first element 2 and the second element 4 on at least one surface, blanketed or structured. This intermediate stage is shown in FIG. 8.

FIG. 9 shows how the connecting layer 6 with a thickness of approximately 300 µm is laminated between the two silicon wafers 52, 54, preferably by the action of pressure between 50 and 500 bar, especially between 200 and 300 bar, and preferably 250 bar, and temperature between 50 and 100°, especially between 60 and 80° and preferably 70°. The connecting layer 6 can be of a glass-containing and especially glass-ceramic material, for example, of an LTCC ceramic. The connecting layer 6 can be laminated in the form of a tape as a green compact. The connecting layer 6 flows under the lamination pressure through the plasticizers placed in the tape, and thus, equalizes all spacing tolerances between the silicon wafers 52, 54. The needle structure 56 penetrates into the surface of the connecting layer 6.

The structuring of the tape and/or of the silicon wafers ensures the removal of organics from the tape in the debinding process through added channels. The flatness defects of the elements 2, 4, especially in the production in a panel, are mitigated by the connecting layer 6, especially by its properties prior to the sintering process.

FIG. 10 shows the state after sintering that takes place at a temperature of more than 600°, preferably more than 750° and, for example, between 800 and 900°. The glass components of the connecting layer 6 combine with all components of the ceramic-containing tape as well as with the nanostructure 56 of the silicon wafers 52, 54. The application of pressure during the sintering process essentially or even completely stops lateral shrinkage of the glass ceramic. The shrinkage perpendicular to the surface of the silicon wafers 52, 54 is about 50% so that in the end the connecting layer 6 is present in a thickness of approximately 150 µm.

While one embodiment has been chosen to illustrate the invention, it will be understood by those skilled in the art that various changes and modifications can be made therein without departing from the scope of the invention as defined in the appended claims.

What is claimed is:

1. A measuring cell for infrared analysis, comprising:
   a flow channel for fluid formed between first and second elements transparent to infrared radiation at least in sections thereof, infrared radiation being able to radiate through said first element into said flow channel and then exit said flow channel through said second element, said first and second elements being connected to each other in a fluid-tight manner;
   a connecting layer disposed between and connecting said first and second elements with very high mechanical strength and being of a sintered glass ceramic material and structured as a ceramic film, said connector layer defining a shape of said flow channel with said first and second elements; and
   a surface of at least one of said first and second elements bordering said flow channel and in an area of said connecting layer and including a surface structure, said surface structure having plurality of microneedles with a density of more than 10,000 microneedles per square millimeter, said surface structure limiting said flow channel and functioning as at least one of an antireflective layer and a filter layer for infrared radiation, said surface structure in said area of said connecting layer functioning as an adhesive agent attaching said one of said first and second elements to said connecting layer.

2. A measuring cell according to claim 1 wherein fluid in said flow channel has a pressure of more than 20 bar.

3. A measuring cell according to claim 1 wherein fluid in said flow channel has a pressure of more than 50 bar.

4. A measuring cell according to claim 1 wherein said connecting layer is applied in a structure manner to said one of said elements.

5. A measuring cell according to claim 1 wherein said connecting layer has discharge channels discharging organic components from said connecting layer in a process preceding sintering thereof.

6. A measuring cell according to claim 1 wherein said connecting layer comprises a low temperature co-fired ceramic having plastifiers.

7. A measuring cell according to claim 1 wherein said connecting layer has a thermal expansion coefficient within a temperature range between 0° and 200° Celsius of less than 5 ppm/K and more than 3 ppm/K.

8. A measuring cell according to claim 1 wherein said connecting layer has a thermal expansion coefficient within a temperature range between 0° and 400° Celsius of less than 5 ppm/K and more than 3 ppm/K.

9. A measuring cell according to claim 1 wherein said connecting layer has a thermal expansion coefficient within a temperature range between 0° and 600° Celsius of less than 5 ppm/K and more than 3 ppm/K.

10. A measuring cell according to claim 1 wherein said density is more than 100,000 microneedles per square millimeter.

11. A measuring cell according to claim 10 wherein said density is more than 500,000 microneedles per square millimeter.

12. A measuring cell according to claim 1 wherein said microneedles have a length greater than 0.3 µm and less than 30 µm.

13. A measuring cell according to claim 1 wherein said microneedles have a length greater than 0.5 µm and less than 15 µm.

14. A measuring cell according to claim 1 wherein said microneedles have a length greater than 0.8 µm and less than 8 µm.

15. A measuring cell according to claim 1 wherein said first and second elements comprise monocrystalline silicon.

16. A measuring cell according to claim 1 wherein said one of said elements has a thickness greater than 1.0 millimeter.

17. A measuring cell according to claim 1 wherein said one of said elements has a thickness greater than 1.5 millimeters.

18. A measuring cell according to claim 1 wherein said one of said elements has a thickness greater than 2.0 millimeters.

19. A measuring cell according to claim 1 wherein microfluidic structures are incorporated in at least one of said first and second elements.

20. A measuring cell according to claim 19 wherein said microfluidic structures are incorporated in a silicon water forming said elements.

21. A measuring cell according to claim 1 wherein microfluidic structures are incorporated in each of said first and second elements.

22. A measuring cell according to claim 21 wherein said microfluidic structures are incorporated in a silicon water forming said elements.

23. A measuring cell according to claim 1 wherein an emitter for infrared radiation and a receiver for infrared radiation are coupled to said first and second elements.

24. A measuring cell according to claim 23 wherein said first and second elements are inserted in a receiving opening of an adjustment element, said adjustment element having an inlet opening and an outlet opening for fluid flow into and out of said fluid channel, respectively.

25. A method of producing a measuring cell, comprising the steps of:
   forming a flow channel for fluid between first and second elements transparent to infrared radiation at least in sections thereof, infrared radiation being able to radiate through the first element into the flow channel and then exit the flow channel through the second element, the first and second elements being connected to each other in a fluid-tight manner;
   disposing a connecting layer between and connecting the first and second elements with very high mechanical strength, the connecting layer being of a sintered glass ceramic material and structured as a ceramic film, the connector layer defining a shape of the flow channel with the first and second elements; and providing a surface of at least one of the first and second elements bordering the flow channel and in an area of the connecting layer and including a surface structure, the surface structure having plurality of microneedles with a density of more than 10,000 microneedles per square millimeter, the surface structure limiting the flow channel and functioning as at least one of an antireflective layer and a filter layer for infrared radiation, the surface structure in the area of the connecting layer functioning as an adhesive agent attaching the one of the first and second elements to the connecting layer;

disposing the connecting layer in an unsintered state between the first and second elements to form an assembly; and sintering the assembly by temperature and pressure.

\* \* \* \* \*